(12) United States Patent  (10) Patent No.: US 8,403,939 B2
Kortenbach  (45) Date of Patent: Mar. 26, 2013

(54) SURGICAL DRILL GUIDE

(75) Inventor: Juergen Kortenbach, Miami Springs, FL (US)

(73) Assignee: Biomet, C.V., Gibraltar (GI)

( * ) Notice: Subject to any disclaimer, the term of this patent is extended or adjusted under 35 U.S.C. 154(b) by 216 days.

(21) Appl. No.: 12/940,071

(22) Filed: Nov. 5, 2010

(65) Prior Publication Data

US 2012/0116410 A1    May 10, 2012

(51) Int. Cl.
  *A61B 17/58* (2006.01)
  *A61B 17/60* (2006.01)
  *A61F 2/00* (2006.01)
(52) U.S. Cl. ............................................ 606/96; 606/98
(58) Field of Classification Search .............. 606/96–98, 606/88
  See application file for complete search history.

(56) References Cited

U.S. PATENT DOCUMENTS

| | | | |
|---|---|---|---|
| 3,664,022 A | 5/1972 | Small | |
| 4,257,411 A | 3/1981 | Cho | |
| 4,901,711 A | 2/1990 | Goble et al. | |
| 5,112,337 A | 5/1992 | Paulos et al. | |
| 5,163,940 A | 11/1992 | Bourque | |
| 5,312,409 A | 5/1994 | McLaughlin et al. | |
| 5,350,380 A | 9/1994 | Goble et al. | |
| 5,354,300 A | 10/1994 | Goble et al. | |
| 5,458,602 A | 10/1995 | Goble et al. | |
| 5,643,273 A | 7/1997 | Clark | |
| 5,968,050 A | 10/1999 | Torrie | |
| 6,210,415 B1 | 4/2001 | Bester | |
| 6,254,604 B1 | 7/2001 | Howell | |
| 6,254,605 B1 | 7/2001 | Howell | |
| 6,869,434 B2 | 3/2005 | Choi | |
| 7,175,632 B2 | 2/2007 | Singhatat et al. | |
| 7,192,432 B2 | 3/2007 | Wetzler et al. | |
| 7,270,666 B2 | 9/2007 | Lombardo et al. | |
| 7,299,561 B2 | 11/2007 | Castaneda | |
| 2003/0216742 A1* | 11/2003 | Wetzler et al. | 606/96 |
| 2005/0149044 A1 | 7/2005 | Justin et al. | |
| 2007/0191855 A1 | 8/2007 | Orbay et al. | |

FOREIGN PATENT DOCUMENTS

EP   1275346   1/2003
WO   WO 2009/134520   11/2009

* cited by examiner

*Primary Examiner* — Andrew Yang
(74) *Attorney, Agent, or Firm* — Harness, Dickey

(57) ABSTRACT

A drill guide system is provided for forming a hole along a desired trajectory in the bone of a surgical patient. The drill guide system comprises a drill bit defining a drill bit axis and a drill guide comprising a frame having a proximal arm and a distal arm fixedly spaced apart. The drill guide further comprises a first guide portion extending from the proximal arm and including a first channel defining a first guide axis, and a pointer projecting proximally from the distal arm and aligned with the first guide axis. The drill bit is transversely insertable into the first channel into an operational position in which the drill bit is constrained to translate only along the first guide axis.

20 Claims, 5 Drawing Sheets

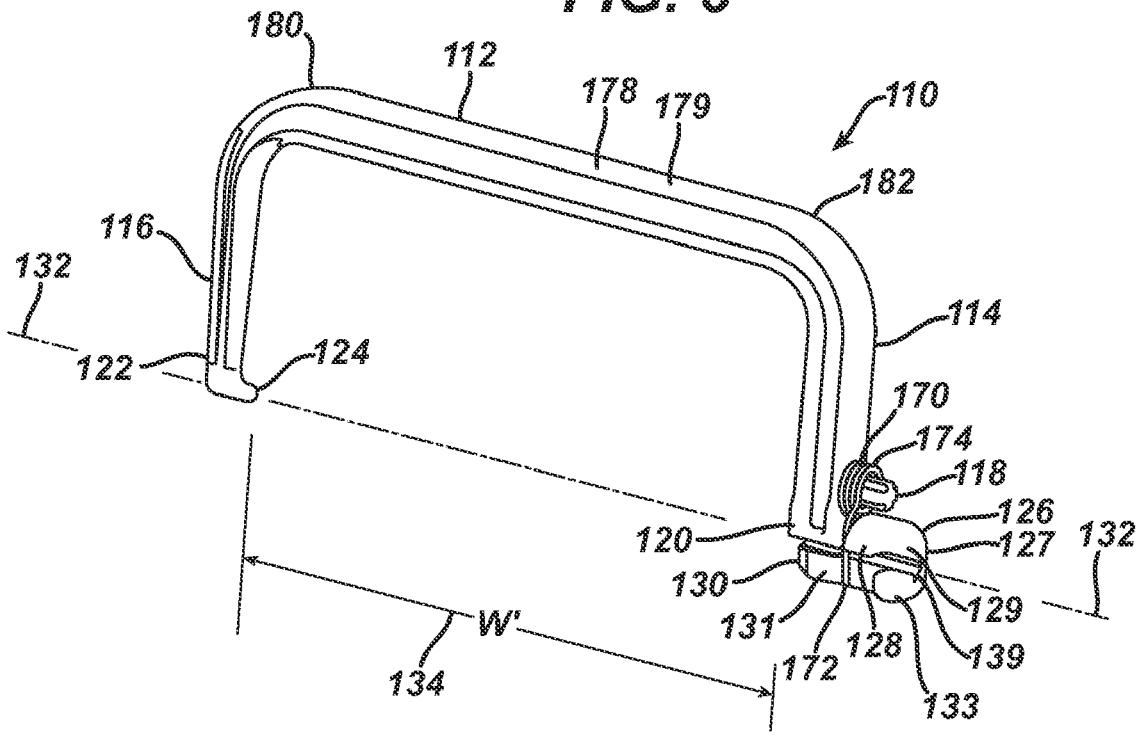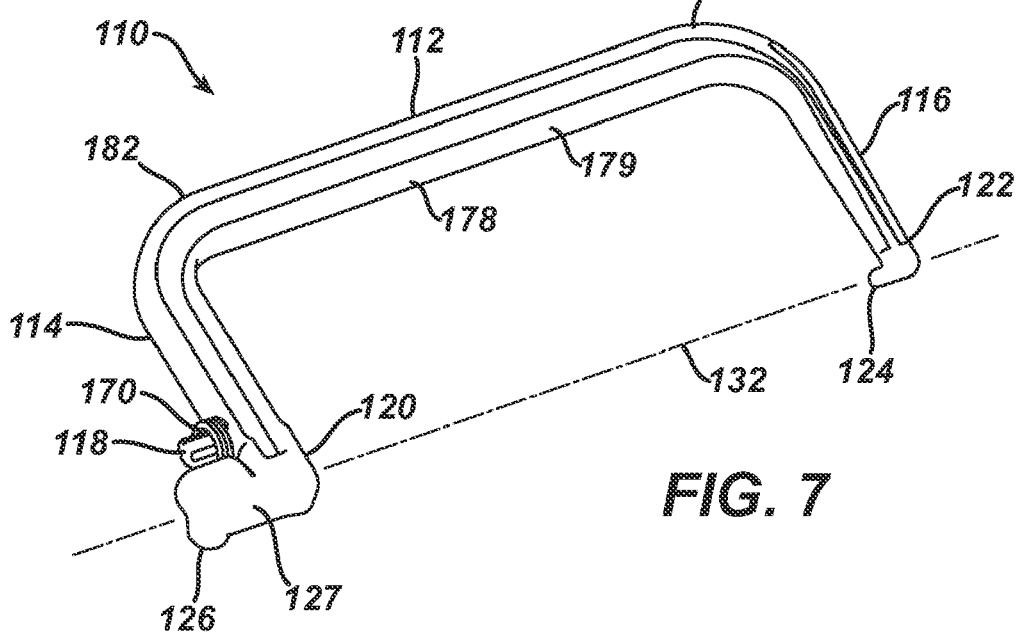

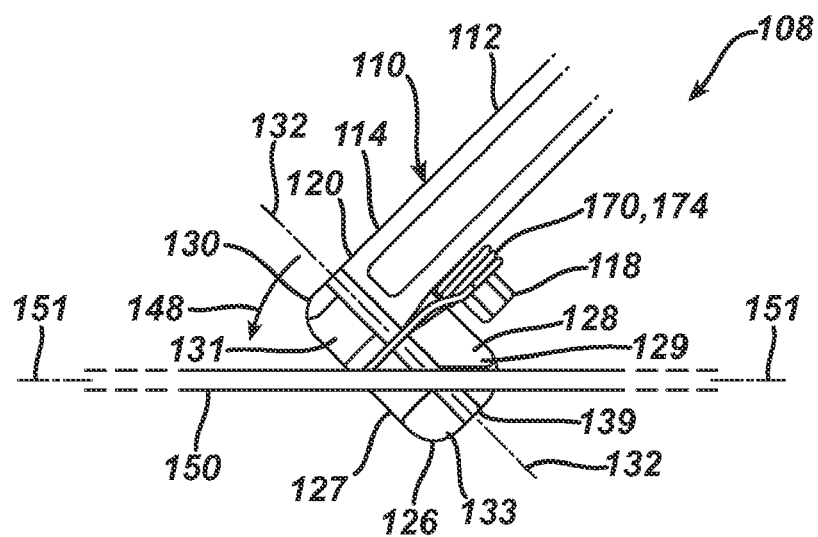
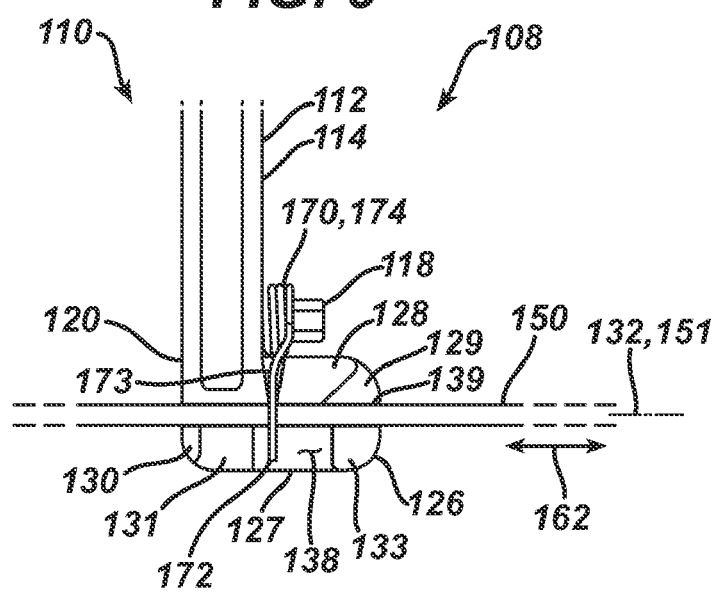
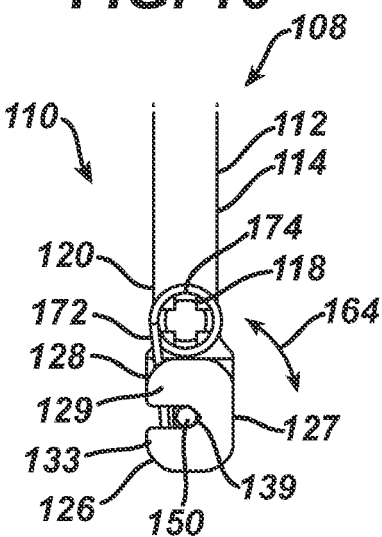

SURGICAL DRILL GUIDE

BACKGROUND

This disclosure relates generally to surgical devices and procedures, and more particularly, to orthopaedic surgical instruments.

During a typical surgical procedure for the internal fixation of a fractured bone, the orthopaedic surgeon attaches a metal bone plate to the bone with a number of bone fasteners, which may include screws, pegs, cables, and other types of fasteners. Before inserting the fastener, the surgeon must drill a properly sized hole at least partially into the bone, taking care to drill along a trajectory that allows good engagement of the fastener into the bone, avoids injury to adjacent soft tissues, and steers clear of other fasteners and structures.

The manufacturers of the many different bone plating systems currently available generally provide surgical drill guides for the surgeon to use with bone drill bits in order to drill the fastener holes. Some of these guides only can indicate the drill trajectory from the front, drill entry side of the bone. However, surgeons often need to visualize the exit location of a hole drilled through the bone to avoid injury to other tissues and structures on the back side of the bone. Other guides include proximal and distal structures for positioning on the front and back side of the bone, respectively, to indicate the entry and exit locations of the drilling trajectory, but these guides may include intricate mechanical components for adjusting the distance between the proximal and distal components. Some of these guides may be used for only one size drill bit so that it is necessary for the surgeon to switch guides when drilling a number of different diameter holes into the bone. Many guides require the surgeon to pass the drill bit tip through a guiding bore or channel of the guide prior to positioning the drill bit tip against the front side of the bone, such that the guide may not be removed from the surgical site until the drill bit is removed from the guide. In some situations, such guides may obstruct the surgeon's vision of important tissues and structures in the surgical site during drilling, when all the surgeons really need is to understand the drill trajectory through the bone for the initial portion of the drilling, after which point the drill bit normally follows along the same trajectory without the aid of the guide.

BRIEF DESCRIPTION OF FIGURES

While this specification concludes with claims that particularly point out and distinctly claim the invention, the following description and the accompanying figures further illustrate some non-limiting examples of the claimed invention. Unless otherwise indicated, like reference numerals identify the same elements.

The devices and descriptions that follow refer specifically to orthopaedic surgical procedures for the internal fixation of fractured bones, although it should be understood that they also may refer to other types of surgical procedures in which it is necessary to drill a hole along a desired trajectory into the bone of a patient.

FIG. 6 is a perspective view of another embodiment of a drill guide, showing the side that receives a drill bit;

FIG. 7 is a perspective view of the opposite side of the drill guide of FIG. 6;

FIG. 8 is a detail view of a guide portion of the drill guide of FIG. 6, shown as a user may initially position it into an intermediate position with respect to the drill bit prior to drilling a hole into bone;

FIG. 9 is a detail view of the guide portion of the drill guide of FIG. 6, shown as a user may finally position it into an operational position with respect to the drill bit prior to drilling a hole into bone; and FIG. 10 is an end view of the guide portion in the operational position as shown in FIG. 9.

SUMMARY

Figure 1:
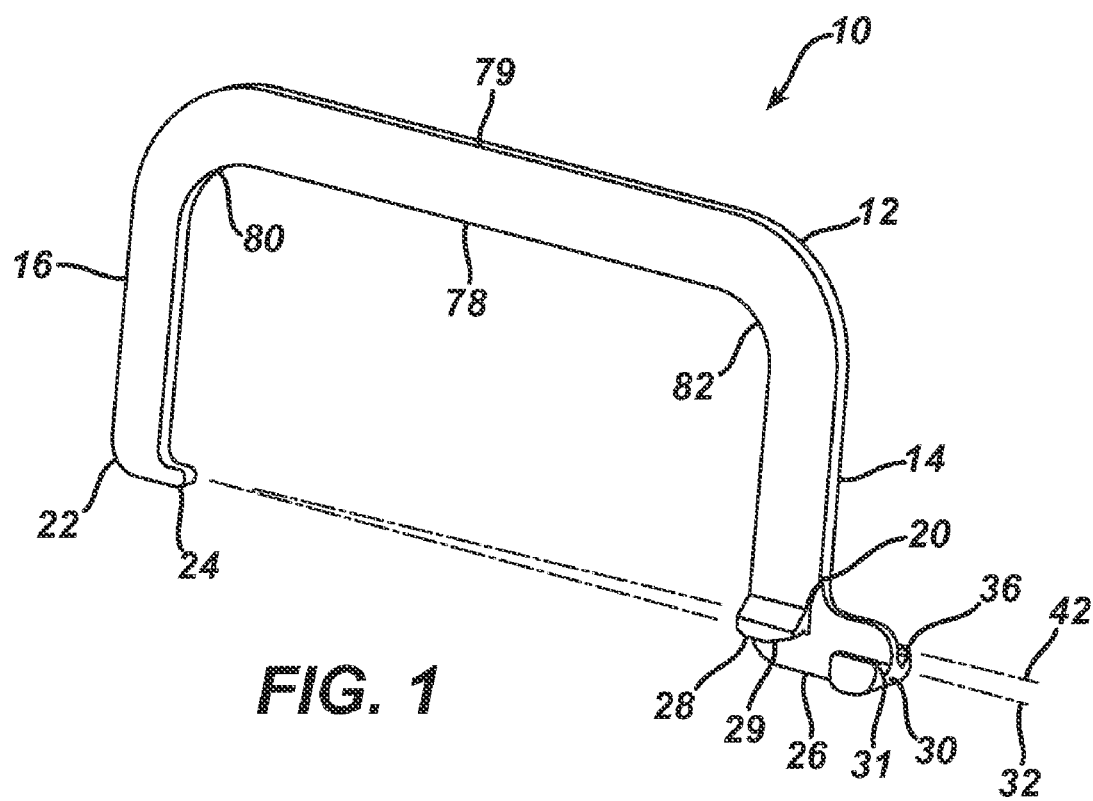
FIG. 1 is a perspective view of a drill guide, showing the side that includes a first guide portion.

A drill guide system for forming a hole along a desired trajectory in the bone of a surgical patient comprises a drill bit defining a drill bit axis and a drill guide comprising a frame having a proximal arm and a distal arm fixedly spaced apart. The drill guide further comprises a first guide portion extending from the proximal arm and including a first channel defining a first guide axis, and a pointer projecting proximally from the distal arm and aligned with the first guide axis. The drill bit is transversely insertable into the first channel into an operational position in which the drill bit is constrained to translate only along the first guide axis.

The drill bit may be transversely removable from the first channel when the drill bit is in the operational position. The first guide portion may further comprise at least two, axially offset guide elements that bound each of the opposing sides of the first channel. The proximal arm and the first guide axis may define a pivot plane, and the drill bit may be transversely insertable into the operational position only by first positioning the drill bit between the guide elements into an intermediate position at which the first guide axis and the drill bit axis define a side-loading angle, and then pivoting the drill guide in the pivot plane until the drill bit is in the operational position. The drill bit may be transversely removable from the operational position only by first pivoting the drill guide in the pivot plane until the drill bit is in the intermediate position. The drill guide may further include a spring element mounted on the proximal arm, and the spring element may have a tail extending across the first channel, such that when the drill bit is in the operational position, the tail exerts a spring force onto the drill bit in a transverse direction with respect to the drill bit axis, thereby holding the drill bit within the first channel. The first channel may have a substantially V-shaped cross section for receiving the drill bit, and the drill bit may have any one of a number of different diameter sizes. The drill guide system may include a plurality of drill bits, each of which has a drill bit diameter size that is approximately in the range of 2.0 mm to 3.5 mm. The drill guide may further comprises a second guide portion having an approximately mirror configuration of the first guide portion and defining a second guide axis that extends through the pointer, and the first and second guide portions extend transversely with respect to the first and second guide axes from opposing sides of the proximal arm. The frame may include a grip area between the proximal and distal arms. The drill guide may be formed from a polymer.

A drill guide for use with a surgical drill bit comprises a generally C-shaped frame having a proximal arm and a distal arm fixedly spaced apart. The drill guide further comprises a guide portion associated with the proximal arm and including a channel defining a guide axis, a lateral opening adapted to side load the drill bit into the channel, and a spring element adapted to retain the drill bit in the channel. The drill guide further comprises a pointer projecting proximally from the distal arm and aligned with the guide axis. The drill bit is transversely insertable into the channel into an operational position in which the drill bit is constrained to translate only along the guide axis, and the drill bit is transversely removable from the channel when the drill bit is in the operational position.

The guide portion may further comprise at least two, axially offset guide elements that define the lateral opening and that bound each of the opposing sides of the channel. The proximal arm and the guide axis may define a pivot plane, and the drill bit may be transversely insertable into the operational position only by first positioning the drill bit between the guide elements into an intermediate position at which the guide axis and the drill bit axis define a side-loading angle, and then pivoting the drill guide in the pivot plane until the drill bit is in the operational position. The drill guide may be transversely removable from the operational position only by first pivoting the drill guide in the pivot plane until the drill bit is in the intermediate position. The spring element may have a tail extending across the channel, such that when the drill bit is in the operational position in the channel, the tail exerts a spring force onto the drill bit in a transverse direction with respect to the axis of the drill bit. The channel may have a substantially V-shaped cross section that is sized to receive a drill bit having any one of a number of drill bits having different diameters. The frame may include a grip area between the proximal and distal arms. The C-shaped frame, guide portion and pointer may be integrally formed from a polymer.

A drill guide for use with a surgical drill bit comprises a non-metallic frame having a proximal arm and a distal arm fixedly spaced apart. The drill guide further comprises a guide portion extending from the proximal arm and including a V-shaped channel defining a guide axis, a pointer projecting proximally from the distal arm and aligned with the guide axis, and a torque spring mounted on the proximal arm and including a tail that extends across the V-shaped channel. The drill bit is transversely insertable into the V-shaped channel into an operational position in which the drill bit is constrained to translate only along the guide axis and the tail exerts a spring force onto the drill bit in a transverse direction with respect to the axis of the drill bit, thereby holding the drill bit within the V-shaped channel. The drill bit is transversely removable from the V-shaped channel when the drill bit is in the operational position.

The frame, the guide portion and the pointer may be integrally formed from a polymer.

DETAILED DESCRIPTION

In this disclosure, the term "user" refers to a surgeon or anyone who may assist the surgeon during a surgical procedure. The term "disposable" as used herein means that it is practical to discard the device after using it in only one surgical procedure.

Figure 2:
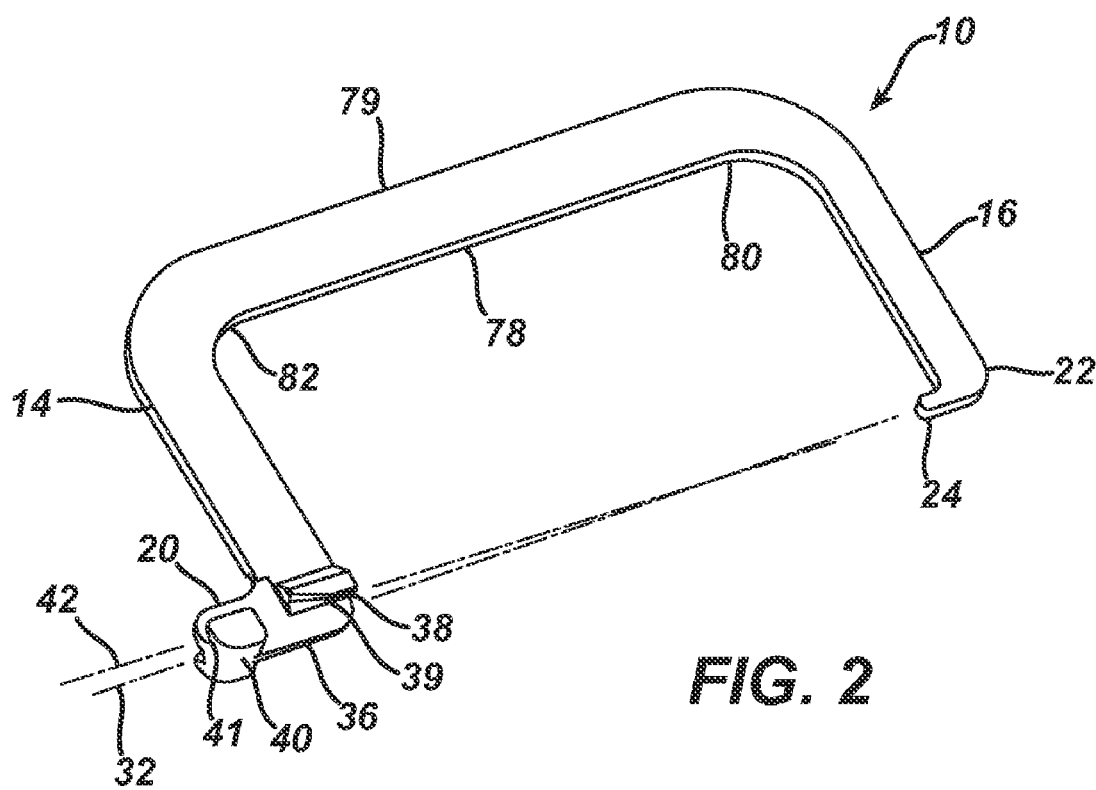
FIG. 2 is a perspective view of the drill guide of FIG. 1, showing the side that includes a second guide portion.

FIG. 1 and FIG. 2 are perspective views of opposite sides of a drill guide 10 that includes a frame 12, a first guide portion 26, a second guide portion 36, and a pointer 24. Frame 12 may be configured generally in a C-shape and may include a beam 78 having a grip portion 79, a distal end 80 and a proximal end 82. A proximal arm 14 may extend from proximal end 82 of beam 78. A distal arm 16 may extend from distal end 80 of beam 78. First guide portion 26 and second guide portion 36 may extend inwardly from a free end 20 of proximal arm 14 towards distal arm 16. First guide portion 26 and second guide portion 36 may be adjacent and extending from opposing sides of proximal arm 14, as shown in FIGS. 1 and 2. Pointer 24 may extend inwardly from a free end 22 of distal arm 16 towards proximal arm 14.

Drill guide 10 may be formed from a metal such as a stainless steel or from any one of a number of other biocompatible, rigid polymers, including, for example, polycarbonate, polyetherimide, and polysulfone. Drill guide 10 may be formed using any one of a number of high volume manufacturing techniques, including injection molding, thereby allowing drill guide 10 to be offered as a relatively low cost, disposable device, as compared to some reusable drill guides currently available.

Still referring to FIGS. 1 and 2, first guide portion 26 defines a first axis 32 and second guide portion defines a second axis 42 that intersects first axis 32 at pointer 24. First guide portion 26 may include a first upper guide element 28 having a first upper channel 29, and a first lower channel element 30 with a first lower channel 31. First upper guide element 28 is spaced apart from first lower guide element 30 along first axis 32. The open sides of first upper channel 29 and first lower channel 31 are offset and face each other. Similarly, second guide portion 36 may include a second upper guide element 38 having a second upper channel 39, and a second lower guide element 40 having a second lower channel 41. Second upper guide element 38 is spaced apart from second lower guide element 40 along second axis 42. The open sides of second upper channel 39 and second lower channel 41 face each other. At least a portion of each of channels 29, 31, 39 and 41 may have a V-shaped, cross-sectional profile, as shown in FIGS. 1 and 2, although a U-shaped and other shaped profiles are also possible.

Figure 3:
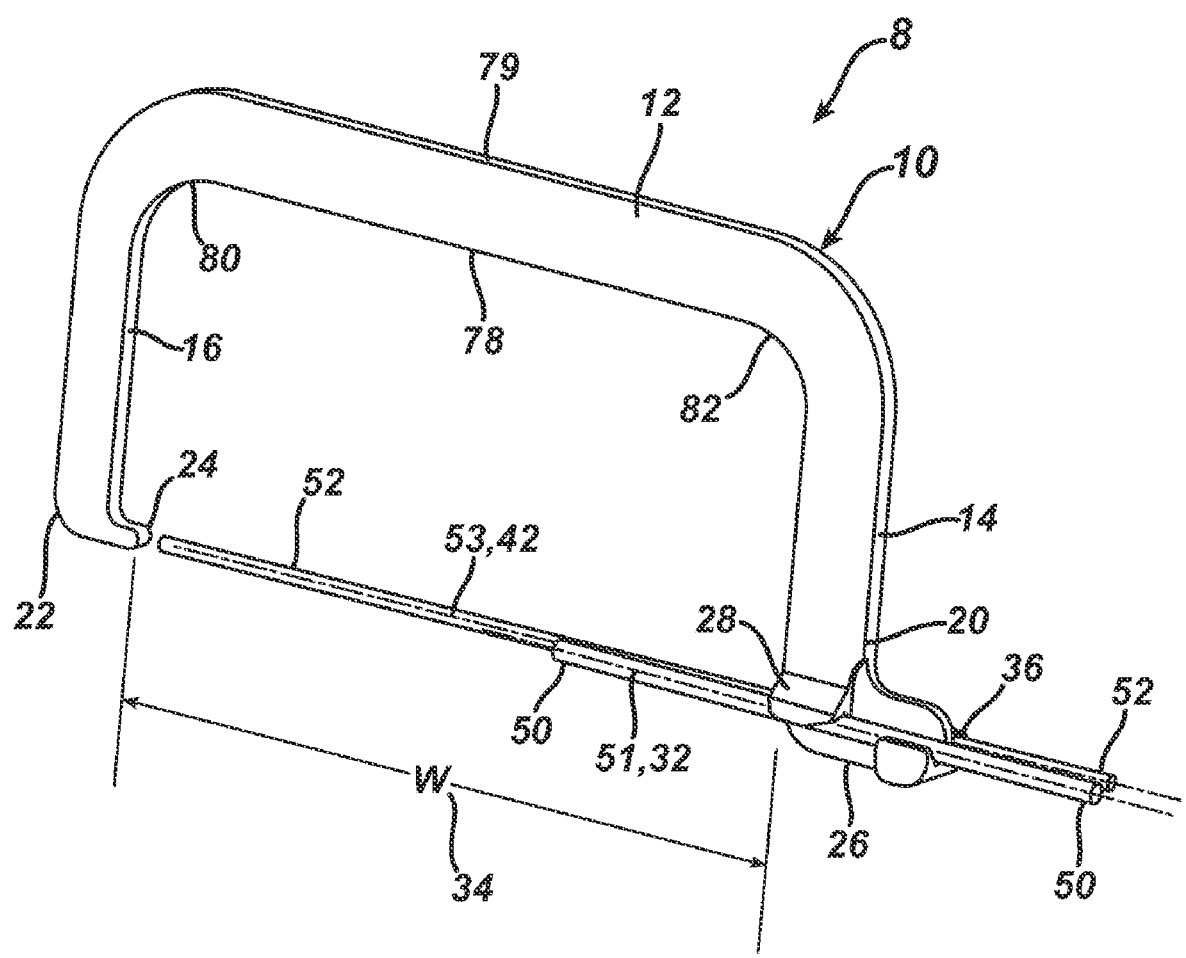
FIG. 3 is a perspective view of a drill guide system, including the drill guide of FIG. 1, showing the side that includes the first guide portion, and also showing for descriptive purposes, representations of a first drill bit positioned in the first guide portion and a second drill bit positioned in the second guide portion, although in actual use, only one of the first and second drill bits may be so located at a time.

FIG. 3 is a perspective view of a drill guide system 8, including drill guide 10, a first drill bit 50 defining a first bit axis 51, and a second drill bit 52 defining a second drill bit axis 53. For descriptive purposes, a representation of first drill bit 50 is shown positioned in first guide portion 26 and a representation of second drill bit 52 is shown positioned in second guide portion 36. In actual use, only one of the drill bits may be so located at a time. The dimensions of first guide portion 26 may be different than the dimensions of second guide portion 36. First drill bit 50 may be used to form a first hole size in the bone and second drill bit 52 may be used to create a second hole size that is different than the first hole size. For example, first drill bit 50 may be a conventional, fluted type of bit that forms a 2.7 mm pilot hole for a 3.5 mm bone fastener. Second drill bit 52 may be, for example, a conventional, 2.0 mm K-wire. As indicated by the graphics on each side of proximal arm 14, first guide portion 26 may be dimensioned to guide first drill bit 50 to form a 2.7 mm hole, and second guide portion 36 may be dimensioned to guide second drill bit 52, which is a 2.0 mm K-wire.

As shown in FIG. 3, frame 12 may be configured to define a bone spanning width 34 between pointer 24 and guide portions 26 and 36. A user may hold drill guide 12 on grip area 79 and position pointer 24 on the back side of the bone, while guide portions 26 and 36 are positioned on the front side of the bone. The user may then visualize the trajectory of the bone drill passing through the bone, wherein the pointer accurately indicates the exit location of the drill through the back side of the bone. In this way, the user can direct the drill bit along a desired trajectory into the bone and avoid injury to soft tissues on the back side of the bone. A number of drill guide 12 may be provided, such as in a kit, each having a unique, bone spanning width, to accommodate different types of bone fractures and patient anatomies. In addition, a number of drill guide 12 may be provided, each uniquely configured to guide different size combinations of drill bits.

As described next for FIGS. 4 and 5, the user may transversely insert ("side load") and transversely remove a drill bit into either one of guide portions 26 and 36. That is, the user may couple the drill guide to the shank of the drill bit by bringing them together in a direction that is approximately perpendicular to the drilling direction, such that the guide axis and the drill bit axis are approximately coaxial.

Figure 4:
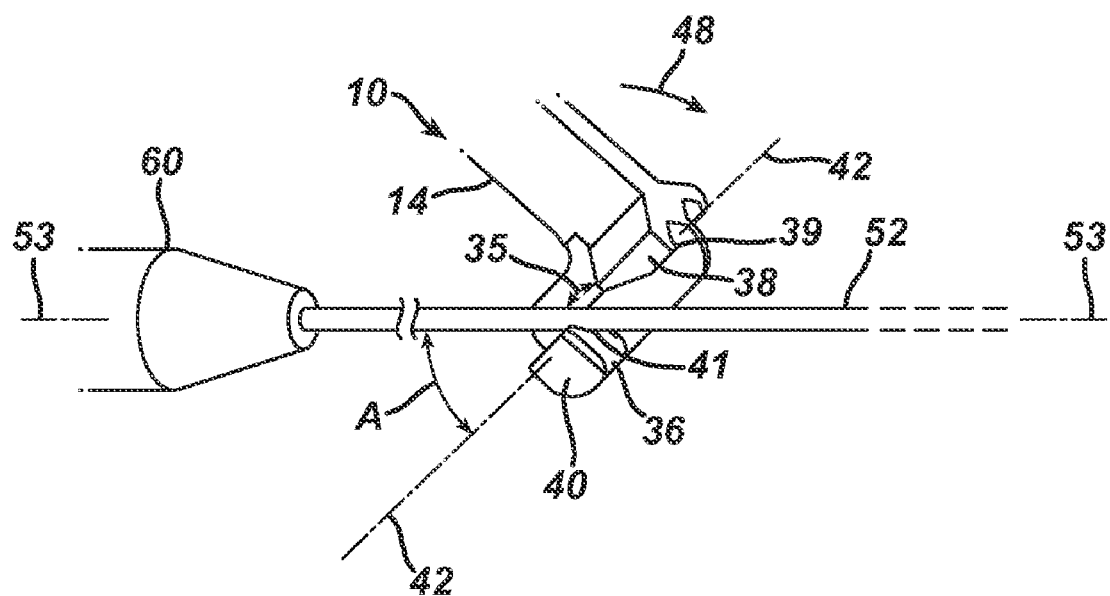
FIG. 4 is a detail view of the second guide portion, shown as a user may initially position it onto the second drill bit prior to drilling a hole into bone.
Figure 5:
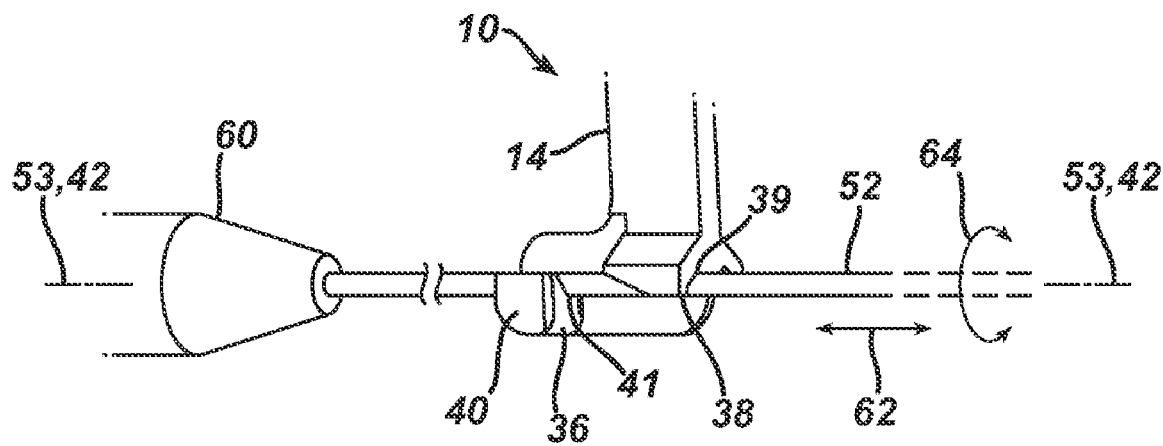
FIG. 5 is a detail view of the second guide portion, shown as a user may finally position it onto the second drill bit prior to drilling a hole into bone.

FIG. 4 is a detail view of an intermediate position of second guide portion 36, shown as a user may initially position it with respect to second drill bit 52 prior to drilling a hole into bone. FIG. 5 is a detail view of an operational position of second guide portion 36, shown as a user may finally position it with respect to second drill bit 52 prior to and during the drilling of a hole into bone.

A key feature of drill guide 10 is the ability of the user to position it onto the drill bit while the tip of the drill bit is already positioned against or partially into the front surface of the bone. Each of first guide portion 26 and second guide portion 36 are configured to "side-load" onto the appropriately sized drill bit. As shown in FIG. 4, for example, a drill motor 60 may be operationally engaged to the proximal end of drill bit 52, and the distal tip of drill bit 52 (not shown) may be against or partially into the bone. The user may then hold drill guide 10, such that second axis 42 of second guide portion 36 is angled with respect to drill bit axis 53, thereby defining a "side-loading angle", indicated by the letter "A" in FIG. 4. Then the user may position drill bit 52 in a lateral opening 35 between second upper guide element 38 and second lower guide element 40. Next the user may rotate drill guide 12 approximately within the pivot plane, (proximal arm 14 and first guide axis 32 define the pivot plane), until second drill bit 52 is captured between second upper channel 39 and second lower channel 41. At this point, second axis 42 is coaxially aligned with drill bit axis 53, and drill guide 12 and drill bit 52 may be moved together to an orientation relative to the bone, such that drill bit axis 53 is directed along a desired trajectory through the bone. When drill bit 52 is fully seated into second drill guide portion 36, drill bit is constrained (as indicated by directional arrows 62 and 64 in FIG. 5) only to translation along axis 42 and to rotation in about axis 42. The user may hold drill guide 12 while drilling the entire length of the hole, or may choose to drill only a portion of the hole, and then remove drill guide 12 using the reverse of the steps just described, before continuing with the drilling.

FIGS. 6 and 7 are perspective views of another embodiment of a drill guide 110 for use with a drill bit when drilling a hole into bone. Drill guide 110 includes a frame 112, a guide portion 126 and a pointer 124. Frame 112 may be configured to resemble a C-clamp and may include a beam 178 having a grip portion 179, a distal end 180 and a proximal end 182. A proximal arm 114 may extend from proximal end 182 of beam 178. A distal arm 116 may extend from distal end 180 of beam 178. Guide portion 126 may extend inwardly from a free end 120 of proximal arm 114 towards distal arm 116. Pointer 124 may extend inwardly from a free end 122 of distal arm 116 towards proximal arm 114.

Drill guide 110 may be formed from a metal such as a stainless steel or from any one of a number of other biocompatible, rigid polymers, including, for example, polycarbonate, polyetherimide, and polysulfone. Frame 112, guide portion 126, and pointer 124 may be integrally formed from a polymer, using any one of a number of high volume manufacturing techniques, including injection molding, thereby potentially enabling drill guide 110 to be offered as a relatively low cost, disposable device.

FIG. 8 is a detail view of guide portion 126 of drill guide 110 of FIG. 6, shown as a user may initially position it onto a drill bit 150 prior to drilling a hole into bone. FIG. 9 is a detail view of guide portion 126 as a user may finally position it onto drill bit 150 prior to drilling a hole into bone. FIG. 10 is an end view of guide portion 126 finally positioned onto drill bit 150 as shown in FIG. 9.

Referring now to FIGS. 6, 7, 8, 9 and 10 in combination, a drill guide system 108 includes drill guide 110 and at least one drill bit 150. Guide portion 126 of drill guide 110 further includes a body 127 extending from end 120 of proximal arm 114. Body 127 has an alignment surface 138 (see FIG. 9) that contains a guide channel 139 defining a guide axis 132. The cross-sectional shape of guide channel 139 may be a V-shape, such that guide channel 139 may receive and guide drill bit 150, and the diameter of drill bit 150 may vary within a drill bit diameter range. For example, the diameter of drill bit 150 may be approximately in the range of 2.7 mm to 3.5 mm. Guide axis 132 aligns with pointer 124 on distal arm 116.

As may be viewed most easily in FIGS. 8 and 9, guide portion 126 includes an upper element 128 having a ramp surface 129 and extending from surface 138 of body 127. Guide portion 126 also includes a first lower element 130 having a ramp 131 and a second lower element 133 spaced apart from first lower element 130. Upper element 128 aligns along one side of channel 139, and first lower element 130 and second lower element 133 align along the opposite side of channel 139. When channel 139 guidingly receives drill bit 150, upper element 128 may be likened to a person's thumb, and first and second lower elements 130, 133 may be likened to a pair of opposing fingers, thereby "holding" drill bit 150 with three points of support. Guide portion 126 also includes a torque spring 170 (or spring element) mounted on a post 118 that extends distally from proximal arm 114. Torque spring 170 may be formed from a metal wire. One end of torque spring 170 forms a tail 172 that extends over channel 139 at approximately a right angle with respect to guide axis 132. Torque spring 170 may be lightly preloaded such that tail 172 exerts a small force against a spring stop 173 (FIG. 9). When channel 139 guidingly receives drill bit 150, tail 142 captures and holds drill bit 150 against channel 139, while allowing free movement in a translational direction 162 and a rotational direction 164.

Like for the previous embodiment (drill guide 10), drill guide 110 is a side-loading device, i.e., a user may operationally position drill guide 110 onto drill bit 150 and also remove drill guide 110 from drill bit 150 even when the drilling tip of drill bit 150 is partially penetrated into bone. Another way to describe this arrangement is that drill bit 150 is transversely insertable into and transversely removable from drill guide 150. It is possible to couple drill bit 150 and drill guide 110 into the operational position by moving either one towards the other. (We predict that normally the user will position drill guide 110 onto drill bit 150, since drill guide 110 is much lighter and easier to manipulate than drill bit 150 attached to the drill motor, and since the tip of drill bit 150 may already be partially inserted into the bone.) As shown in FIG. 8, to clip drill guide 110 onto drill bit 150, the user holds drill guide 110, such that guide axis 132 is angled with respect to drill bit axis 151. Then the user positions drill bit 150 against surface 138 and in the lateral opening between first and second lower elements 131, 133, and pivots drill guide 110 in the pivot plane defined by proximal arm 114 and guide axis 132, as indicated by arrow 148, such that guide axis 132 becomes aligned with drill bit axis 151, as shown in FIG. 9. As the user pivots drill guide 110, drill bit 150 slides on ramps 129, 131 and becomes captured under tail 172 of torque spring 170.

Drill guide 110 is very lightweight since it may be formed from a lightweight material such as plastic. Therefore, once the user clips drill guide 110 onto drill bit 150 in the operational position such as shown in FIG. 9, and then positions the tip of drill bit 150 on the near surface of the bone, the user may move the position of pointer 124 on the far side of the bone simply by orientation of the surgical drill. The user may clip drill guide 110 on and off of drill bit 150 at practically any point during the drilling procedure. For example, the user may choose to remove drill guide 110 from drill bit 150 after drilling about halfway through the bone, in order to focus on watching the far surface of the bone while the tip of drill bit 150 breaks through the bone surface.

We also envision providing a kit containing a plurality of drill guides, wherein each drill guide may have a unique, bone spanning width between the proximal and distal arms, and/or each drill guide may be sized to receive a unique range of drill bit sizes. The kit may also include a plurality of drill bits of various types and sizes.

We have shown and described various embodiments and examples. However, a person having ordinary skill in the art may modify the methods and devices described herein without departing from the overall concept. For instance, the specific materials, dimensions and the scale of drawings should be understood to be non-limiting examples. Accordingly, we do not intend the scope of the following claims to be understood as limited to the details of structure, materials or acts shown and described in the specification and drawings.

I claim:

1. A drill guide system for forming a hole along a desired trajectory in the bone of a surgical patient, the drill guide system comprising:
    a drill bit defining a drill bit axis; and
    a drill guide comprising a frame having a proximal arm and a distal arm fixedly spaced apart, a first guide portion extending from the proximal arm and including a first channel defining a first guide axis, and a pointer projecting proximally from the distal arm and aligned with the first guide axis;
    wherein the drill bit is transversely insertable into the first channel into an operational position in which the drill bit is constrained to translate only along the first guide axis;
    wherein the proximal arm and the first guide axis define a pivot plane, and the drill bit is transversely insertable into the operational position by first positioning the drill bit into an intermediate position at which the first guide axis and the drill bit axis define a side-loading angle, and then pivoting the drill guide in the pivot plane until the drill bit is in the operational position.

2. The drill guide system of claim 1, wherein the drill bit is transversely removable from the first channel when the drill bit is in the operational position.

3. The drill guide system of claim 2, wherein the first guide portion further comprises at least two, axially offset guide elements that bound each of the opposing sides of the first channel.

4. The drill guide system of claim 3, wherein the drill bit is positioned between the guide elements in the intermediate position.

5. The drill guide system of claim 4, wherein the drill bit is transversely removable from the operational position only by first pivoting the drill guide in the pivot plane until the drill bit is in the intermediate position.

6. The drill guide of claim 1, wherein the drill guide further includes a spring element mounted on the proximal arm, and the spring element has a tail extending across the first channel, such that when the drill bit is in the operational position, the tail exerts a spring force onto the drill bit in a transverse direction with respect to the drill bit axis, thereby holding the drill bit within the first channel.

7. The drill guide system of claim 1, wherein the first channel has a substantially V-shaped cross section for receiving the drill bit, and the drill bit can have any one of a number of different diameter sizes.

8. The drill guide system of claim 1, further including a plurality of drill bits, each of which has a drill bit diameter size that is approximately in the range of 2.0 mm to 35 mm.

9. The drill guide system of claim 1, wherein the drill guide further comprises a second guide portion having an approximately mirror configuration of the first guide portion and defining a second guide axis that extends through the pointer, and the first and second guide portions extend transversely with respect to the first and second guide axes from opposing sides of the proximal arm.

10. The drill guide system of claim 1, wherein the frame includes a grip area between the proximal and distal arms.

11. The drill guide system of claim 1, wherein the drill guide is formed from a polymer.

12. A drill guide for use with a surgical drill bit, the drill guide comprising:
    a generally C-shaped frame having a proximal arm and a distal arm fixedly spaced apart;
    a guide portion associated with the proximal arm and including a channel defining a guide axis, a lateral opening adapted to side load the drill bit into the channel, and a spring element adapted to retain the drill bit in the channel; and
    a pointer projecting proximally from the distal arm and aligned with the guide axis;
    wherein the drill bit is transversely insertable into the channel into an operational position in which the drill bit is constrained to translate only along the guide axis, and the drill bit is transversely removable from the channel when the drill bit is in the operational position;
    wherein the proximal arm and the guide axis define a pivot plane, and the drill bit is transversely insertable into the operational position by first positioning the drill bit into an intermediate position at which the guide axis and the drill bit axis define a side-loading angle, and then pivoting the drill guide in the pivot plane until the drill bit is in the operational position.

13. The drill guide of claim 12, wherein the guide portion further comprises at least two, axially offset guide elements that define the lateral opening and that bound each of the opposing sides of the channel.

14. The drill guide of claim 13, wherein the drill bit is positioned between the guide elements in the intermediate position, and the drill guide is transversely removable from the operational position only by first pivoting the drill guide in the pivot plane until the drill bit is in the intermediate position.

15. The drill guide of claim 12, wherein the spring element has a tail extending across the channel, such that when the drill bit is in the operational position in the channel, the tail exerts a spring force onto the drill bit in a transverse direction with respect to the axis of the drill bit.

16. The drill guide system of claim 12, wherein the channel has a substantially V-shaped cross section that is sized to receive a drill bit having any one of a number of drill bits having different diameters.

17. The drill guide system of claim 12, wherein the frame includes a grip area between the proximal and distal arms.

18. The drill guide system of claim 12, wherein the drill guide is formed from a polymer.

19. A drill guide for use with a surgical drill bit, the drill guide comprising:
- a non-metallic frame having a proximal arm and a distal arm fixedly spaced apart;
- a guide portion extending from the proximal arm and including a V-shaped channel defining a guide axis;
- a pointer projecting proximally from the distal arm and aligned with the guide axis; and
- a torque spring mounted on the proximal arm and including a tail that extends across the V-shaped channel;
- wherein the drill bit is transversely insertable into the V-shaped channel into an operational position in which the drill bit is constrained to translate only along the guide axis and the tail exerts a spring force onto the drill bit in a transverse direction with respect to the axis of the drill bit, thereby holding the drill bit within the V-shaped channel, and the drill bit is transversely removable from the V-shaped channel when the drill bit is in the operational position;
- wherein the proximal arm and the guide axis define a pivot plane, and the drill bit is transversely insertable into the operational position only by first positioning the drill bit into an intermediate position at which the guide axis and the drill bit axis define a side-loading angel, and then pivoting the drill guide in the pivot plane until the drill bit is in the operational position.

20. The drill guide of claim 19, wherein the frame, the guide portion and the pointer are integrally formed from a polymer.

\* \* \* \* \*

UNITED STATES PATENT AND TRADEMARK OFFICE
CERTIFICATE OF CORRECTION

| | | |
|---|---|---|
| PATENT NO. | : 8,403,939 B2 | Page 1 of 1 |
| APPLICATION NO. | : 12/940071 | |
| DATED | : March 26, 2013 | |
| INVENTOR(S) | : Juergen Kortenbach | |

It is certified that error appears in the above-identified patent and that said Letters Patent is hereby corrected as shown below:

In the Claims

Column 8, line 3, Claim 8, delete "35" and insert --3.5--, therefor

Column 10, line 12, Claim 19, delete "angel" and insert --angle--, therefor

Signed and Sealed this
Fourth Day of November, 2014

Michelle K. Lee
*Deputy Director of the United States Patent and Trademark Office*